United States Patent [19]

Trick

[11] 4,369,771
[45] Jan. 25, 1983

[54] PENILE ERECTILE SYSTEM

[75] Inventor: Robert E. Trick, Racine, Wis.

[73] Assignee: Medical Engineering Corporation, Racine, Wis.

[21] Appl. No.: 305,048

[22] Filed: Sep. 24, 1981

[51] Int. Cl.$^3$ .............................................. A61F 5/00
[52] U.S. Cl. ..................................................... 128/79
[58] Field of Search ................................. 128/79; 3/1

[56] References Cited

U.S. PATENT DOCUMENTS

| | | | |
|---|---|---|---|
| 3,853,122 | 12/1974 | Strauch et al. | 128/79 |
| 3,954,102 | 5/1976 | Buuck | 128/79 |
| 4,009,711 | 3/1977 | Uson | 128/79 |
| 4,066,073 | 1/1978 | Finney et al. | 128/79 |
| 4,201,202 | 5/1980 | Finney et al. | 128/79 |
| 4,267,829 | 5/1981 | Burton | 128/79 |

Primary Examiner—Dalton L. Truluck
Attorney, Agent, or Firm—Quarles & Brady

[57] ABSTRACT

A simple, reliable pressure control valve for a medical device having a hydraulic system comprises a valve housing having an open top and a bottom and an inwardly directed shoulder partially closing the top; a poppet with an upwardly extending stem mounted in the housing between the top and the bottom; a sealing edge mounted on the poppet circumferentially about the stem, and a calibrated spring urging the poppet towards the open top of the housing so that the sealing edge is in sealing contact with the underside of said shoulder and the stem extends above the top of said housing so that manual pressure can be exerted upon the stem to open the valve or the valve can be opened by a hydraulic pressure which exerts sufficient force upon the top of the poppet to overcome the force of the spring.

2 Claims, 7 Drawing Figures

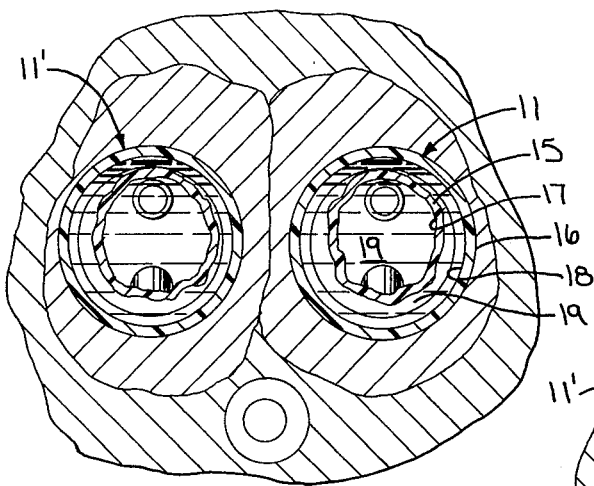
FIG. 3
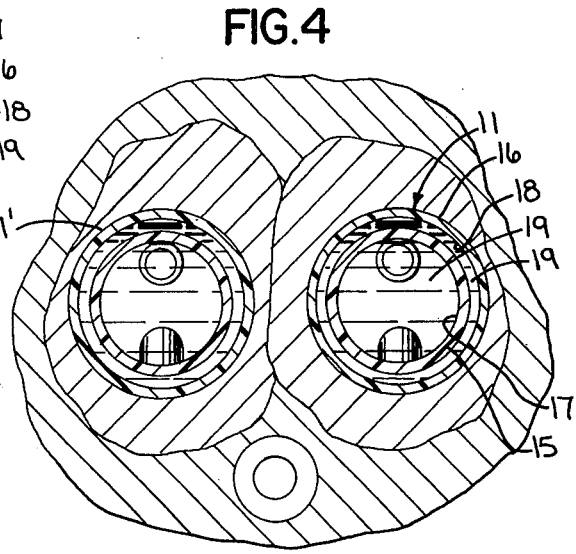
FIG. 4
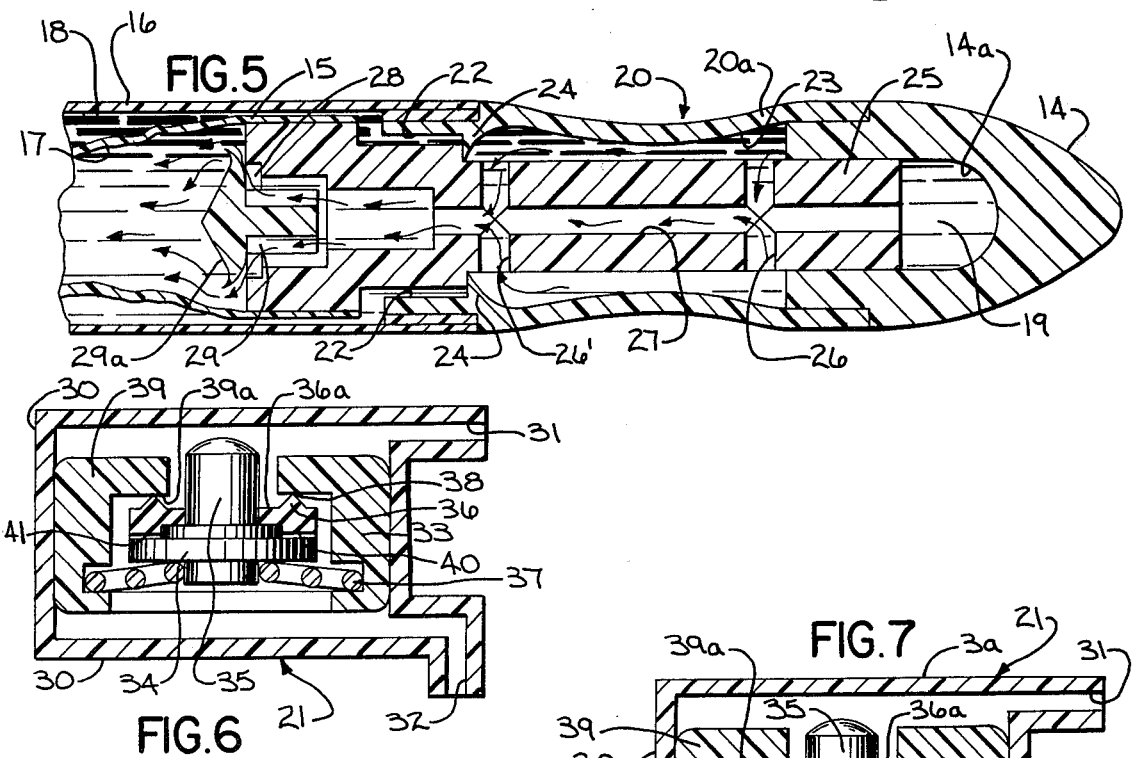
FIG. 5
FIG. 6
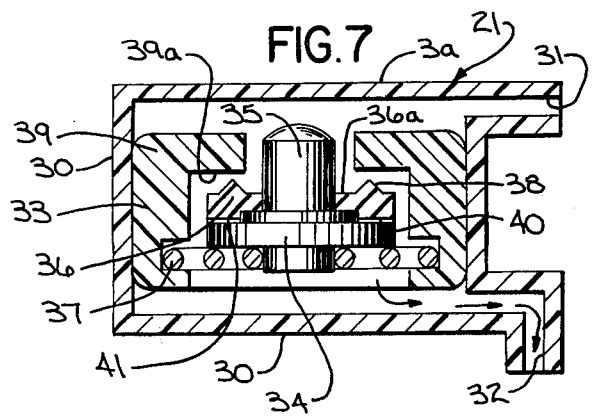
FIG. 7

PENILE ERECTILE SYSTEM

The present invention relates to a penile erectile system. More particularly, it relates to an inflatable, implantable penile erectile system having a simple, effective pressure control valve.

DESCRIPTION OF THE PRIOR ART

There are some cases of erectile impotence for which the surgical implantation of a penile erectile system is the only practical means of remedying the impotency. In such cases in the past, several different types of implantable penile erectile systems have been employed.

One type of implantable penile erectile system which has been employed is an inflatable system which includes two inflatable and distensible tubes each of which is surgically implanted in a separate corporus cavernosum of the penis. Each of the tubes is connected by tubing to a relatively large reservoir of inflating and pressurizing fluid which is implanted elsewhere in the body necessitating additional abdominal surgery. An erection is achieved by inflating and pressurizing the distensible tubes. The devices of U.S. Pat. No. 3,954,102 and U.S. Pat. No. 4,009,711 are representative of inflatable penile erectile systems.

Another type of penile erectile system comprises a pair of rods of suitable stiffness which are surgically implanted into the corpora cavernosa of the penis. A significant advantage of this system is that the amount of surgery involved is minimal as there is no pressure bulb to implant. A disadvantage of this system is that the permanent stiffness of the rods can be a source of physical pain and embarrassment to the patient. Representative penile erectile systems employing rod implants are disclosed in U.S. Pat. No. 3,893,476 and U.S. Pat. No. 4,066,037.

Another implantable erectile system which combines some of the features of both the inflatable system and the rod implant system is disclosed in U.S. Pat. No. 4,201,202. The system disclosed therein includes a rod within a sleeve positioned about the rod to form a chamber. An erection is achieved by pressurizing the chamber to straighten and support the rod and the chamber is depressurized by use of a pressure control valve.

SUMMARY OF THE INVENTION

It is the general object of the present invention to disclose an implantable pressurizable penile erectile system which includes a reliable, relatively inexpensive pressure control valve.

It is a further object to disclose a penile erectile system which has a pressure control valve which automatically opens when a predetermined hydraulic pressure is exceeded in the system and which also can be manually operated from the outside to deflate or depressurize the system.

In the preferred embodiment of the present invention the penile erectile system consists of two identical, independent self-contained, pressurizable implants which can be surgically implanted completely within the penis as easily as implanting a rod type implant.

The implants of the preferred embodiment of the penile erectile system of the present invention each have a relatively short, proximal stem portion, a distal tip portion, and an elongated flexible intermediate portion containing a pair of concentric cylindrical chambers. The two chambers are connected by a passage so that hydraulic fluid present in the outer chamber can be transferred to the inner non-distensible chamber to pressurize it and make it rigid. The system also includes pump means for transferring fluid under pressure from the outer chamber to the inner chamber and a pressure control valve which can be used to both prevent the pressure in the inner chamber from exceeding a predetermined pressure and to depressurize or deflate the inner chamber.

The pressure control valve of the present invention which can be opened manually and also will open automatically when a predetermined hydraulic pressure exists in the inner chamber is positioned in the passage between the two chambers and comprises a valve jacket having an inlet and an outlet, a valve housing positioned in the jacket, a poppet having a base, an upward extending stem, and a sealing edge circumferentially positioned about the stem mounted in the housing and a spring or equivalent means for urging the sealing edge on the poppet into sealing contact with a seat, then closing off flow between the inner and outer chambers until pressure on the poppet overcomes the force of the spring or equivalent means and the sealing edge is moved off the seat.

The preferred implants, which contain all the components of the penile erectile system, can be implanted in the corpora cavernosa in the same manner as penile rod implants. When the preferred implants are in place, the inner chambers of the implants are pressurized by pumping the hydraulic fluid from the outer chambers into the non-distensible inner chambers under pressure causing them to become rigid and the penis to assume an erectile position. The inner chambers are depressurized by activating the pressure control valve.

The penile erectile system of the present invention, in addition to being compact and thus minimizing the amount of surgery required, also has the advantage of having a minimum number of fluid connections, thus reducing the risk of leakage.

The foregoing and other objects and advantages will become apparent from the description which follows:

BRIEF DESCRIPTION OF THE DRAWINGS

FIG. 3 is an enlarged cross sectional view taken along the line 3—3 in FIG. 1;

FIG. 4 is an enlarged cross sectional view taken along the line 4—4 in FIG. 2;

FIG. 5 is an enlarged view, partly in section, of the tip portion of the implant of FIG. 1 showing the positions of the pump components when the pump is being used to pressurize the inner chamber;

FIG. 6 is an enlarged view of the pressure control valve showing the positions of the valve components when the valve is closed; and FIG. 7 is a view similar to FIG. 6 showing the positions of the valve components when the valve is open.

DESCRIPTION OF THE PREFERRED EMBODIMENTS

Figure 1:
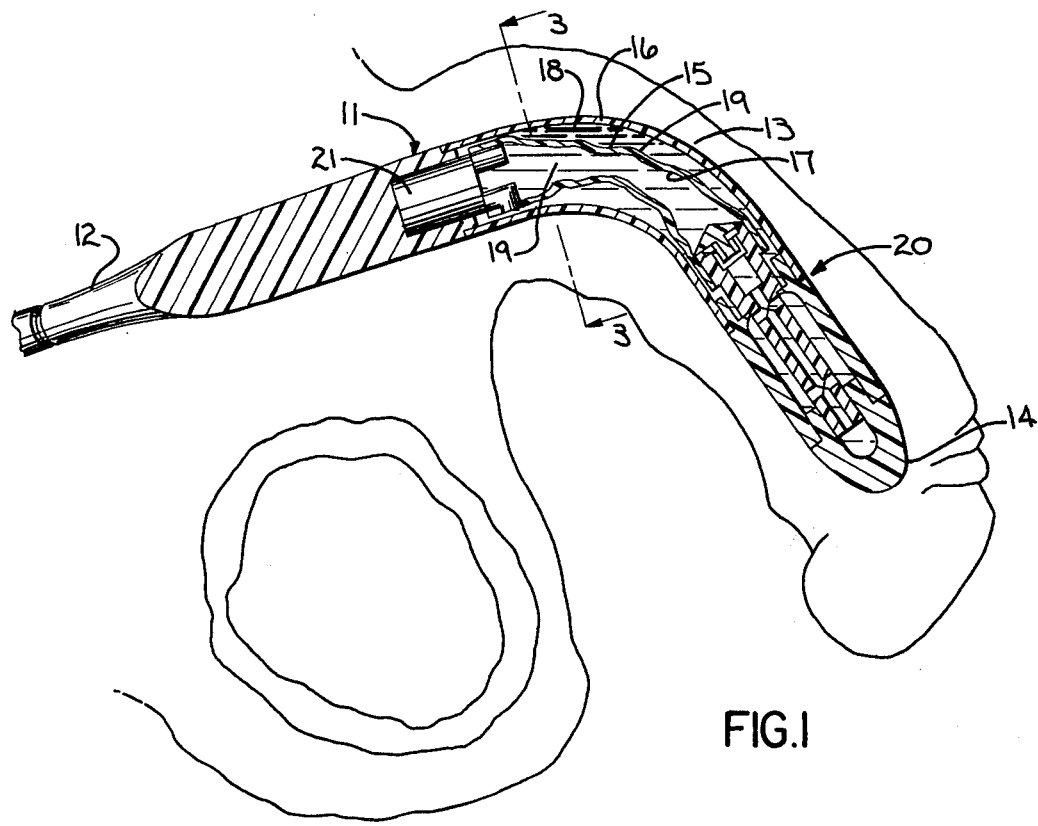
FIG. 1 is a side view, partly in section, of the preferred embodiment of the penile erectile system of the present invention showing one of the two identical penile implants surgically implanted in a male and in a non-pressurized condition.

The preferred embodiment of the penile erectile system of the present invention, which is shown in the drawings, comprises a pair of elongated penile implants 11, 11'. The two implants 11, 11' are identical, therefore, only one will be described in detail.

Figure 2:
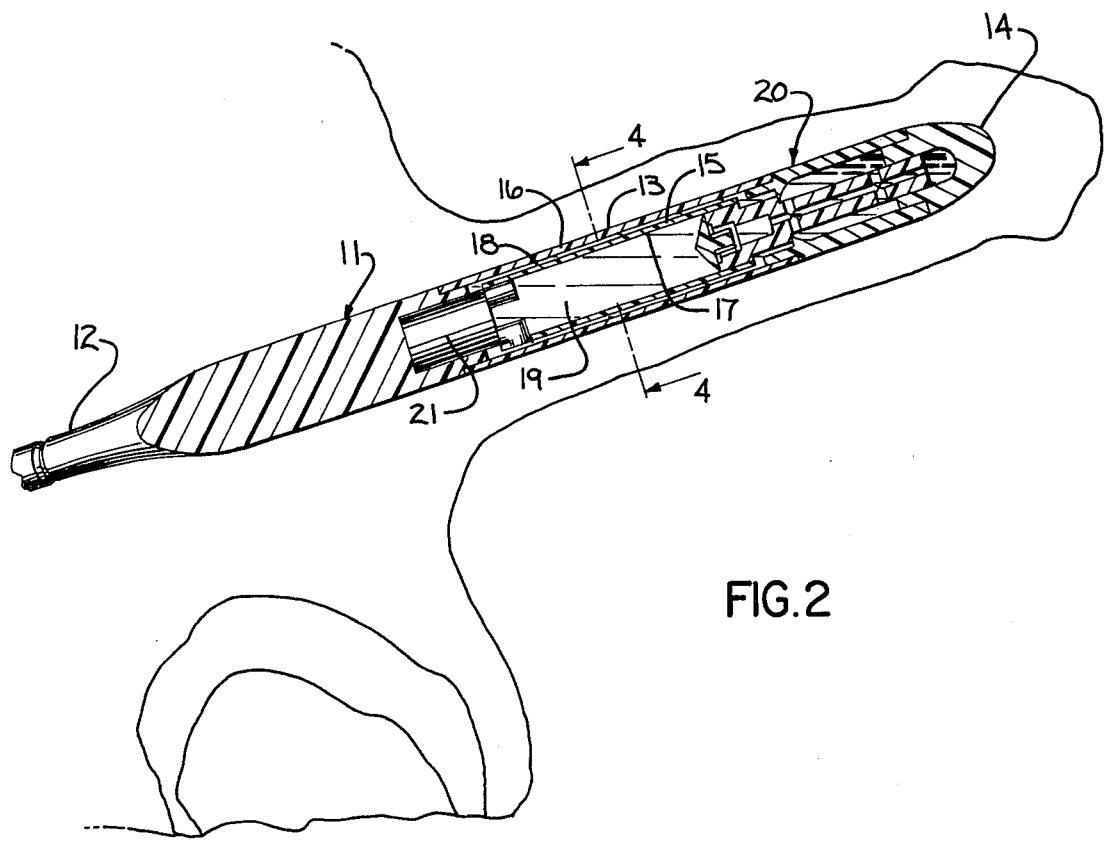
FIG. 2 is a side view similar to FIG. 1, except that the implant is pressurized.

As seen best in FIGS. 1 and 2, the implant 11 has a proximal stem portion 12, an intermediate cylindrical portion 13, and a distal tip portion 14. The stem portion 12 which is of a relatively stiff material is implanted in the root end of a corpus cavernosum and the intermediate cylindrical portion 13 and the tip portion 14 which are soft and relatively flexible are implanted in the portion of the corpus cavernosum in the pendulous penis. As seen in FIGS. 3 and 4, each of the implants 11, 11' is positioned in a separate corpus cavernosum of the penis.

The intermediate cylindrical portion 13 of the implant 11 preferably includes a pair of concentric cylindrical sleeves 15 and 16 which are attached in a fluid tight manner to the stem portion 12 and to the tip portion 14 to form a pair of concentric chambers 17 and 18, respectively. The sleeve 15 which forms the wall of the inner chamber 17 is of a relatively inelastic material such as a silicone coated mesh or woven fabric so that the chamber 17 is non-distensible even when pressurized. The sleeve 15 cooperates with the sleeve 16 which is spaced outwardly from the sleeve 15 to form the outer chamber 18. The sleeve 16 may be made of a distensible material such as nonreinforced silicone rubber. The necessary fluid tight seals between the sleeves 15 and 16 and the stem portion 12 and tip portion 14 may be made with a suitable adhesive or by other suitable means.

As seen in FIGS. 1 and 3, when the implant 11 is in a non-pressurized state both the chambers 17 and 18 are substantially filled with a non-compressible hydraulic fluid 19 which may be a biocompatible fluid such as saline or a free flowing silicone gel. In the non-pressurized state, the soft, flexible, intermediate cylindrical portion 13 of the implant 11 flexes and permits the penis to assume a substantially normal, flaccid position as seen in FIG. 1. However, when the implant 11 is in the pressurized state, as seen in FIGS. 2 and 4, the intermediate cylindrical portion 13 is rigid as the result of the non-distensible inner chamber 17 being completely filled with fluid under pressure and the penis assumes an erectile position.

The pump means, generally referred to as 20, for pressurizing the inner chamber 17 and the pressure control valve 21 for limiting the fluid pressure in the chamber 17 will now be described.

As seen best in FIG. 5, there is a passage 22 in the distal tip portion 14 of the implant 11 which leads from the outer chamber 18 to the pumping chamber 23 of the pump 19. As seen therein the exit of the passage 22 is closed by a one way flap valve 24 which only opens when the fluid pressure in the passage 22 exceeds that in the pumping chamber 23.

Positioned within the pumping chamber 23 is a support member 25 which has axial passages 26, 26' and a longitudinal passage 27 extending therethrough. The support member 25 extends from and provides communication between the hollow interior 14a of the conical tip 14, the pumping chamber 23 and the inner chamber 17. The end of the passage 27 opposite the conical tip 14 has an enlarged exit 28 in which there is positioned an umbrella type flexible check valve 29. The check valve 29 is normally kept seated closing the passage 27 by fluid pressure in chamber 17. However, when the wall of the pump 20 is squeezed as shown in FIG. 5 the fluid pressure in the pumping chamber 23 and passage 27 exceeds that in chamber 17 and the edges of the check valve 29 are deflected allowing fluid to flow about the check valve 29 into chamber 17 as indicated by the arrows.

The implant 11 is pressurized by sequentially squeezing the resilient wall 20a of the pump 20 to force the hydraulic fluid 19 from the pumping chamber 23 into non-distensible inner chamber 17 under pressure and then allowing the wall 20a to assume its normal shape. When the pump wall 20a is first squeezed the fluid 19 originally in the pumping chamber 23 is forced through the axial passages 26, 26' and longitudinal passage 27 out the exit 28 forcing the edges of the check valve 29 off their seat allowing the fluid 19 to flow about the valve 29 into the chamber 17 (as shown by the arrows in FIG. 5). The increased pressure in the pumping chamber 23 keeps the flap valve 24 seated closing passage 22 and preventing flow into chamber 18. Thereafter, when the wall 20a is allowed to assume its normal position, a reduced pressure is formed in the pumping chamber 23 and as a result the flap valve 24 is moved off its seat allowing fluid 19 to flow from chamber 18 into the pumping chamber 23. Whenever the pressure in pumping chamber 23 equals or exceeds that in chamber 18 the flap valve 24 is seated closing the passage 22. When the chamber 17 is sufficiently pressurized and rigid, the pumping is stopped whereby the exit 28 of the passage 27 is closed by pressure of the fluid 19 in chamber 17 upon the outer surface 29a on the enlarged head of the check valve 29. As a result, the chamber 17 remains filled, pressurized and rigid, as seen in FIG. 2, until the pressure control valve 21 is opened to allow fluid 19 to flow back to the chamber 18 whereupon the implant 11 resumes a non-pressurized state as seen in FIG. 1.

If desired, the filling and pressurizing of the non-distensible inner chamber 17 may be facilitated by manually squeezing the penis to help force fluid 19 which is in chamber 18 through the passage 22, past the flap valve 24 and into the pumping chamber 23.

It will be appreciated that a variety of pump mechanisms other than that shown in the drawing can be used. However, the pump should be of the type which opens which it is squeezed and automatically closes when the squeezing stops.

The preferred pressure control valve 21 may be manually opened and will automatically open when the pressure in the chamber 17 exceeds a predetermined level.

As seen best in FIGS. 6 and 7, the pressure control valve 21 includes an outer jacket 30 having an inlet 31 which communicates with the inner chamber 17 and an outlet 32 which leads to the outer chamber 18. Positioned between the inlet 31 and the outlet 32 is a valve housing 33. A poppet 34 having a stem 35 is movably mounted in the housing 33. As seen in FIG. 6, the poppet 34 which has an annular seal 36 positioned about the stem 35 is supported within the housing 33 by a preloaded spring 37 so that the sharp edge 38 of the seal 36 bears against the flat under surface of a flange 39 which partially closes the top of the housing 33. The force of the spring 37 on the underside of the poppet 34 normally keeps the sharp edge 38 of the seal 36 in fluid tight contact with the flat underside 39a of the flange 39 so that the valve 29 is closed and no fluid can flow from the inlet 31 to the outlet 32 or vice versa.

The valve 21 can be opened to permit fluid to flow from the chamber 17 to the chamber 18 by manually exerting a pressure on the jacket 30 at point 30a to cause the jacket 30 to deflect and contact stem 35 of the poppet 34. Further movement of the jacket 31 causes the poppet 34 to move towards the spring 37 and the seal edge 38 to move from sealing engagement with the underside 39a of the flange 39 of the housing 33 as seen in FIG. 7. As a result, fluid 19 flows from the pressurized inner chamber 17 to the outer chamber 18. When the deflecting pressure on the jacket 31 and the stem 35 is removed the preloaded spring 37 forces the sharp edge 38 back into sealing arrangement with the flat underside 39a of the flange 39 cutting off flow from the inlet 31 to the outlet 32.

The valve 21 also serves as a safety valve for the penile implant. When the fluid pressure in the inner chamber 17 exceeds a predetermined safe pressure the pressure sensed on the top surface 36a of the seal 36 exceeds the force of the preloaded spring 37 and the sharp sealing edge 38 is moved out of sealing engagement with the underside 39a of the shoulder 39. Fluid then flows from the inner chamber 17 to the outer chamber 18 until a safe pressure is reached whereupon the spring 37 causes the sharp edge 38 once again into sealing engagement with the underside 39a of the shoulder 39.

In the preferred embodiment of the valve 21 seen best in FIGS. 6 and 7, there are a pair of vents 40 and 41 on the bottom of the seal 36. The vents 40 and 41 keep the bottom area of the seal 36 at low or outer chamber 18 pressure. As a result when a higher pressure which is insufficient to open the valve 21 is applied to the top area of the seal 36 positioned within the boundary of the annular sharp edge 38 the sharp edge 38 is forced into an excellent sealing engagement with the underside 39a of the shoulder 39.

The non-distensible inner chamber 17 of the penile implant when pressurized provides the rigidity required to maintain the penis in an erectile position. Therefore, it must be of sufficient volume and size to perform this function. In contrast, the outer chamber 18 serves primarily as a reservoir of pressurizing fluid for the inner chamber and is sized accordingly. The exact dimensions of the inner and outer chambers are not critical as long as they are adequate to provide their desired function.

The sleeve 15 which forms the wall of the "non-distensible" chamber 17 must be relatively inelastic and is preferably made of a dacron mesh or fabric covered with silicone material that will not stretch when filled with fluid and pressurized. In contrast, the sleeve 16 may be either distensible or non-distensible. The diameters of the sleeves 15 and 16 can vary but are normally sized so that the implant in the non-pressurized state will fill the corpora cavernosa. It will be appreciated that the term non-distensible or inelastic is intended to cover any material which possesses the desired properties which enable it to provide its described function.

The proximal stem portion 12 of the implant preferably has a Shore A hardness of about 70, the distal tip portion 14 a Shore A hardness of about 20, and each of the materials has sufficient tensile strength for its intended use. In the preferred embodiments of the drawings, the tip is tapered and is made of a self-sealing silicone elastomer which allows fluid to be added to or removed from the implant with a fine hollow needle and a syringe.

The term "substantially filled" as used herein to describe the fluid content of a chamber means that a chamber contains about 60% to about 95% or more of its capacity of a non-compressible fluid such as water, saline or a free flowing gel. The actual content of fluid can vary; however, the implant when "substantially filled" should be still sufficiently flexible so that the penis can assume a normal flaccid position.

All of the parts and components of the prosthesis are preferably made of or covered with medical grade silicone rubber which is non-reactive, non-toxic and well tolerated by the adjacent organic tissues. Silicone rubber is preferred because it is quite resistant to wear and remains functional for long periods of time. However, other suitable materials possessing desirable properties may also be employed.

The preferred method of implantation of the erectile system is through an incision made in the penis. After appropriate incision, each corpus cavernosum is dilated distally and proximally to accept the implants. The appropriate anatomical measurements are made to insure that the proximal stem of the implant or implants will be positioned at the base of the penis below the pelvic bone. An implant or implants having an appropriately sized intermediate section and distal tip is inserted into the corpus cavernosum of the penis. The distal tip is positioned in the glans end of the corpus cavernosum. The proximal stem of the implant then is anchored in the root end of the corpus cavernosum.

The identical procedure is performed on the other side of the penis to complete the surgical procedure. The proximal stems of the two implants preferably will diverge laterally to accommodate the anatomy, to provide lateral stability to the penis and to prevent rotation of the implants. The incision is then closed.

It is to be undersood that the foregoing description has been for purposes of illustration and that a number of modifications and changes may be made without departing from the spirit and scope of the present invention. For example, although the implants described have solid stems for anchoring the implants, the stems could be hollow, if desired. In addition, although implants have been described and illustrated in which the outer chamber which serves as the reservoir is concentric relative to the inner chamber it will be appreciated that the reservoir role could be provided by one or more radially disposed smaller individual outer chambers if desired. Furthermore, in some applications it may be desired that the locations of the pump 20 and the valve 21 be reversed. It also will be appreciated that the inner chamber 17 may contain a rod as shown in U.S. Pat. No. 4,201,202 to reduce its volume or provide additional support. Finally, it will be understood that the novel pressure control valve may be used in other medical device applications.

In view of the foregoing, it is to be understood that the invention is not to be limited by any of the specific embodiments described but only by the claims which follow:

I claim:

1. A penile implant comprising an elongated unitary body having a tip portion at one end, an anchoring stem portion at the other end; an intermediate portion having an inner chamber and a radially disposed outer chamber, said inner chamber being non-distensible so that when pressurized and filled with fluid it becomes rigid; a passage providing communication between said inner and outer chambers; pump means within the body for transferring fluid to the inner chamber to pressurize it and make it rigid; and a pressure control valve for controlling the pressure in said inner chamber, said pressure control valve comprising:

(a) a valve jacket having an inlet and an outlet, said inlet communicating with the inner chamber, and the outlet communicating with the outer chamber;
(b) a valve housing positioned in said jacket, said housing having an open top and bottom and an inwardly directed shoulder partially closing said top;
(c) a poppet mounted in said housing between the inlet and the outlet; said poppet having a base with an upwardly extending stem;
(d) a seal member positioned on top of said poppet, said member having a sealing edge which extends circumferentially about said stem;
(e) means exerting a force upon said poppet urging it toward the open top of the housing so that the sealing edge will be in sealing contact with the underside of the shoulder closing said valve, said valve being openable by exerting manual pressure on the stem to reduce the pressure in the inner chamber of the penile implant and automatically openable when the pressure in the inner chamber exceeds the force exerted on said poppet.

2. The penile implant of claim 1 in which the means exerting a force is a precalibrated spring which permits the valve to open when a predetermined force is sensed by the top of the poppet and automatically closes the valve when the pressure sensed by the top of the poppet is less than the predetermined force.

* * * * *